US008617214B2

(12) United States Patent
Malek

(10) Patent No.: US 8,617,214 B2
(45) Date of Patent: Dec. 31, 2013

(54) SPINAL TENSION BAND

(75) Inventor: Michel H. Malek, Chicago, IL (US)

(73) Assignee: MMSN Limited Partnership, Kankakee, IL (US)

( * ) Notice: Subject to any disclaimer, the term of this patent is extended or adjusted under 35 U.S.C. 154(b) by 903 days.

(21) Appl. No.: 11/970,321

(22) Filed: Jan. 7, 2008

(65) Prior Publication Data

US 2009/0177233 A1 Jul. 9, 2009

(51) Int. Cl.
*A61B 17/70* (2006.01)
(52) U.S. Cl.
USPC .......................................... 606/257; 606/263
(58) Field of Classification Search
USPC .......................................... 606/246, 257, 263
See application file for complete search history.

(56) References Cited

U.S. PATENT DOCUMENTS

| 4,011,602 | A | 3/1977 | Rybicki et al. |
|---|---|---|---|
| 4,349,921 | A | 9/1982 | Kuntz |
| 4,401,112 | A | 8/1983 | Resaian |
| 4,643,178 | A | 2/1987 | Nastari et al. |
| 4,657,550 | A | 4/1987 | Daher |
| 4,743,256 | A | 5/1988 | Brantigan |
| 4,743,260 | A | 5/1988 | Burton |
| 4,759,766 | A | 7/1988 | Büettner-Janz et al. |
| 4,759,769 | A | 7/1988 | Hedman et al. |
| 4,863,476 | A | 9/1989 | Shepperd |
| 4,946,378 | A | 8/1990 | Hirayama et al. |
| 4,946,458 | A | 8/1990 | Harms et al. |
| 4,997,432 | A | 3/1991 | Keller |
| 5,024,670 | A | 6/1991 | Smith et al. |
| 5,084,048 | A | 1/1992 | Jacob et al. |
| 5,092,866 | A | 3/1992 | Breard et al. |
| 5,122,130 | A | 6/1992 | Keller |
| 5,246,458 | A | 9/1993 | Graham |
| 5,258,031 | A | 11/1993 | Salib et al. |
| 5,261,911 | A | 11/1993 | Carl |
| 5,282,863 | A | 2/1994 | Burton |
| 5,306,310 | A | 4/1994 | Siebels |
| 5,314,477 | A | 5/1994 | Marnay |
| 5,314,478 | A | 5/1994 | Oka et al. |
| 5,336,223 | A | 8/1994 | Rogers |
| 5,352,224 | A | 10/1994 | Westermann |

(Continued)

FOREIGN PATENT DOCUMENTS

| DE | 22 63 842 A | 7/1974 |
|---|---|---|
| DE | 30 23 353 A1 | 4/1981 |

(Continued)

OTHER PUBLICATIONS

The International Search Report and Written Opinion for PCT/US2004/032116 mailed on Feb. 16, 2005, 12 pages.

(Continued)

*Primary Examiner* — Ellen C Hammond
(74) *Attorney, Agent, or Firm* — Foley & Lardner LLP

(57) ABSTRACT

Medical apparatuses for restricting the motion of a vertebra relative to another vertebra and methods for using the apparatuses are provided herein. The medical apparatuses comprise a flexible element having two ends and a connector capable of securing the ends of the flexible element to a first vertebra disposed above or below a second vertebra or to a spinal device. The flexible element is disposed across at least a portion of one or more vertebral elements of the second vertebra and is tensioned to restrict the motion of the second vertebra relative to the first vertebra.

10 Claims, 8 Drawing Sheets

(56) References Cited

U.S. PATENT DOCUMENTS

| | | | |
|---|---|---|---|
| 5,375,823 A | 12/1994 | Navas |
| 5,380,324 A | 1/1995 | Müller et al. |
| 5,380,328 A | 1/1995 | Morgan |
| 5,401,269 A | 3/1995 | Büttner-Janz et al. |
| 5,415,659 A | 5/1995 | Lee et al. |
| 5,437,671 A | 8/1995 | Lozier et al. |
| 5,458,641 A | 10/1995 | Ramirez Jimenez |
| 5,496,318 A | 3/1996 | Howland et al. |
| 5,534,029 A | 7/1996 | Shima |
| 5,536,124 A | 7/1996 | Silva |
| 5,540,688 A | 7/1996 | Navas |
| 5,556,431 A | 9/1996 | Büttner-Janz |
| 5,562,738 A | 10/1996 | Boyd et al. |
| 5,591,166 A | 1/1997 | Bernhardt et al. |
| 5,607,425 A | 3/1997 | Rogozinski |
| 5,628,740 A | 5/1997 | Mullane |
| 5,645,596 A | 7/1997 | Kim et al. |
| 5,649,925 A | 7/1997 | Alacreu |
| 5,672,175 A | 9/1997 | Martin |
| 5,688,275 A | 11/1997 | Koros et al. |
| 5,702,453 A | 12/1997 | Rabbe et al. |
| 5,702,455 A | 12/1997 | Saggar |
| 5,713,899 A | 2/1998 | Marnay et al. |
| 5,725,582 A | 3/1998 | Bevan et al. |
| 5,776,198 A | 7/1998 | Rabbe et al. |
| 5,836,948 A | 11/1998 | Zucherman et al. |
| 5,888,226 A | 3/1999 | Rogozinski |
| 5,893,889 A | 4/1999 | Harrington |
| 5,951,553 A | 9/1999 | Betz et al. |
| 5,989,290 A | 11/1999 | Biedermann et al. |
| 6,019,792 A | 2/2000 | Cauthen |
| 6,030,389 A | 2/2000 | Wagner et al. |
| 6,063,121 A | 5/2000 | Xavier et al. |
| 6,074,390 A | 6/2000 | Zucherman et al. |
| 6,083,224 A | 7/2000 | Gertzbein et al. |
| 6,113,637 A | 9/2000 | Gill et al. |
| 6,139,579 A | 10/2000 | Steffee et al. |
| 6,146,421 A | 11/2000 | Gordon et al. |
| 6,179,874 B1 | 1/2001 | Cauthen |
| 6,214,012 B1 | 4/2001 | Karpman et al. |
| 6,217,578 B1 | 4/2001 | Crozet et al. |
| 6,228,118 B1 | 5/2001 | Gordon |
| 6,241,730 B1 | 6/2001 | Alby |
| 6,293,949 B1 | 9/2001 | Justis et al. |
| 6,296,644 B1 | 10/2001 | Saurat et al. |
| 6,296,664 B1 | 10/2001 | Middleton |
| 6,299,613 B1 * | 10/2001 | Ogilvie et al. ............. 606/279 |
| 6,315,797 B1 | 11/2001 | Middleton |
| 6,368,350 B1 | 4/2002 | Erickson et al. |
| 6,375,682 B1 | 4/2002 | Fleischmann et al. |
| 6,375,683 B1 | 4/2002 | Crozet et al. |
| 6,395,034 B1 | 5/2002 | Suddaby |
| 6,402,750 B1 | 6/2002 | Atkinson et al. |
| 6,419,703 B1 | 7/2002 | Fallin et al. |
| 6,436,099 B1 * | 8/2002 | Drewry et al. ............. 606/300 |
| 6,454,807 B1 | 9/2002 | Jackson |
| 6,478,800 B1 | 11/2002 | Fraser et al. |
| 6,500,178 B2 | 12/2002 | Zucherman et al. |
| 6,517,580 B1 | 2/2003 | Ramadan et al. |
| 6,520,990 B1 | 2/2003 | Ray |
| 6,540,785 B1 | 4/2003 | Gill et al. |
| 6,554,831 B1 | 4/2003 | Rivard et al. |
| 6,565,605 B2 | 5/2003 | Goble et al. |
| 6,579,319 B2 | 6/2003 | Goble et al. |
| 6,579,320 B1 | 6/2003 | Gauchet et al. |
| 6,582,466 B1 | 6/2003 | Gauchet |
| 6,582,468 B1 | 6/2003 | Gauchet |
| 6,585,769 B1 | 7/2003 | Muhanna et al. |
| 6,607,558 B2 | 8/2003 | Kuras |
| 6,616,669 B2 * | 9/2003 | Ogilvie et al. ............. 606/279 |
| 6,626,905 B1 | 9/2003 | Schmiel et al. |
| 6,626,908 B2 | 9/2003 | Cooper et al. |
| 6,652,585 B2 | 11/2003 | Lange |
| 6,685,742 B1 | 2/2004 | Jackson |
| 6,695,842 B2 | 2/2004 | Zucherman et al. |
| 6,730,126 B2 | 5/2004 | Boehm et al. |
| 6,752,831 B2 | 6/2004 | Sybert et al. |
| 6,761,720 B1 | 7/2004 | Senegas |
| 6,764,515 B2 | 7/2004 | Ralph et al. |
| 6,835,205 B2 | 12/2004 | Atkinson et al. |
| 6,852,128 B2 | 2/2005 | Lange |
| 6,902,566 B2 | 6/2005 | Zucherman et al. |
| 6,946,000 B2 | 9/2005 | Senegas et al. |
| 6,966,910 B2 | 11/2005 | Ritland |
| 6,966,931 B2 | 11/2005 | Huang |
| 6,989,011 B2 | 1/2006 | Paul et al. |
| 7,022,138 B2 | 4/2006 | Mashburn |
| 7,025,787 B2 | 4/2006 | Bryan et al. |
| 7,041,138 B2 | 5/2006 | Lange |
| 7,044,970 B2 | 5/2006 | Errico et al. |
| 7,056,343 B2 | 6/2006 | Schafer et al. |
| 7,101,375 B2 | 9/2006 | Zucherman et al. |
| 7,147,665 B1 | 12/2006 | Bryan et al. |
| 7,175,623 B2 | 2/2007 | Thramann et al. |
| 7,186,256 B2 | 3/2007 | Michelson |
| 7,201,751 B2 | 4/2007 | Zucherman et al. |
| 7,255,713 B2 | 8/2007 | Malek |
| 7,282,064 B2 | 10/2007 | Chin |
| 7,318,825 B2 | 1/2008 | Butler et al. |
| 7,402,176 B2 | 7/2008 | Malek |
| 2001/0016773 A1 | 8/2001 | Serhan et al. |
| 2001/0029375 A1 | 10/2001 | Betz et al. |
| 2001/0032020 A1 | 10/2001 | Besselink |
| 2001/0037111 A1 | 11/2001 | Dixon et al. |
| 2001/0051829 A1 | 12/2001 | Middleton |
| 2002/0022888 A1 | 2/2002 | Serhan et al. |
| 2002/0107574 A1 | 8/2002 | Boehm, Jr. et al. |
| 2002/0111683 A1 | 8/2002 | Ralph et al. |
| 2002/0147454 A1 | 10/2002 | Neto |
| 2003/0009223 A1 | 1/2003 | Fehling et al. |
| 2003/0009226 A1 | 1/2003 | Graf |
| 2003/0018390 A1 | 1/2003 | Husson |
| 2003/0023312 A1 | 1/2003 | Thalgott |
| 2003/0032958 A1 | 2/2003 | Soubeiran |
| 2003/0055427 A1 | 3/2003 | Graf |
| 2003/0100951 A1 | 5/2003 | Serhan et al. |
| 2003/0176861 A1 | 9/2003 | Reed |
| 2003/0191534 A1 | 10/2003 | Viart et al. |
| 2003/0229348 A1 | 12/2003 | Sevrain |
| 2004/0002762 A1 | 1/2004 | Hawkins |
| 2004/0153156 A1 | 8/2004 | Cohen et al. |
| 2004/0167626 A1 | 8/2004 | Geremakis et al. |
| 2005/0085910 A1 | 4/2005 | Sweeney |
| 2005/0113927 A1 | 5/2005 | Malek |
| 2005/0143823 A1 | 6/2005 | Boyd et al. |
| 2005/0165486 A1 | 7/2005 | Trieu |
| 2005/0209593 A1 | 9/2005 | Kolb |
| 2005/0209697 A1 | 9/2005 | Paponneau et al. |
| 2005/0234425 A1 | 10/2005 | Miller et al. |
| 2006/0036243 A1 | 2/2006 | Sasso et al. |
| 2006/0079895 A1 | 4/2006 | McLeer |
| 2006/0106381 A1 | 5/2006 | Ferree et al. |
| 2006/0161154 A1 | 7/2006 | McAfee |
| 2006/0200140 A1 | 9/2006 | Lange |
| 2006/0224223 A1 | 10/2006 | Podhajsky et al. |
| 2007/0010813 A1 | 1/2007 | Zucherman et al. |
| 2007/0112299 A1 | 5/2007 | Smit et al. |
| 2007/0173937 A1 | 7/2007 | Khalili |
| 2007/0270828 A1 | 11/2007 | Bruneau et al. |
| 2008/0027444 A1 | 1/2008 | Malek |
| 2008/0140122 A1 * | 6/2008 | Bethell ............. 606/263 |
| 2009/0062109 A1 | 3/2009 | Malek |
| 2009/0177233 A1 | 7/2009 | Malek |
| 2009/0204149 A1 | 8/2009 | Malek |
| 2009/0287118 A1 | 11/2009 | Malek |
| 2010/0121378 A1 | 5/2010 | Malek |
| 2010/0160964 A1 | 6/2010 | Malek |

FOREIGN PATENT DOCUMENTS

| | | |
|---|---|---|
| EP | 0 176 728 A | 4/1986 |
| EP | 0 560 140 B1 | 9/1993 |
| EP | 0 560 141 A | 9/1993 |
| EP | 0 566 810 B1 | 10/1993 |

(56) References Cited

FOREIGN PATENT DOCUMENTS

| | | |
|---|---|---|
| FR | 2 694 882 A | 2/1994 |
| FR | 2 801 782 | 12/1999 |
| FR | 2 805 985 | 9/2001 |
| WO | WO 94/04100 | 3/1994 |
| WO | WO 95/26697 | 10/1995 |
| WO | WO 01/06939 | 2/2001 |
| WO | WO 02/24087 | 3/2002 |
| WO | WO 03/094699 | 11/2003 |
| WO | WO 2008/014337 | 1/2008 |
| WO | WO 2009/088746 | 7/2009 |
| WO | WO 2009/100117 | 8/2009 |

OTHER PUBLICATIONS

"Anatomic Facet Replacement System (AFRS™)," *Natural Motion*; published by Facet Solutions, Inc.; http://www.facetsolutions.com/Device.html on or before Nov. 2, 2007.

International Search Report and Written Opinion for PCT International Application No. PCT/US2008/088015 dated Feb. 13, 2009.

European Patent Office Search Report for Application No. 04812086.9, dated Aug. 19, 2011, 5 pages.

* cited by examiner

SPINAL TENSION BAND

FIELD OF THE INVENTION

The invention generally relates to medical apparatuses for the spine. More specifically, medical apparatuses and methods are disclosed which are capable of restricting the motion of a vertebra relative to another vertebra.

BACKGROUND

The human spine comprises individual vertebrae that interlock with each other to form a spinal column. The vertebral elements of a vertebra are labeled in FIG. 1. The vertebra 100 has a vertebral body 102, two pedicles 104 extending from the vertebral body, a lamina 106 extending from the pedicles, and three winglike projections. These winglike projections are the spinous process 108 extending from the lamina and the two transverse processes 110 extending from the pedicles. In addition, the vertebra 100 has two superior articular processes 112 extending from the pedicles and two inferior articular processes 114 extending from the lamina. The articular processes of adjacent vertebrae form the facet joints. The inferior articular process of one vertebra articulates with the superior articular process of the vertebra below. Adjacent vertebrae are separated and cushioned by an intervertebral disc 116.

Together, two adjacent vertebrae, their facet joints, the intervertebral disc and the connecting ligament tissue make up a motion segment unit, the smallest portion of the spine that exhibits kinematic behavior characteristic of the entire spine. The motion segment unit is capable of flexion, extension, rotation, lateral bending and translation and each component of the unit contributes to the mechanical stability of the entire unit. Trauma, degeneration, aging, disease, surgery, and the like may damage any of the components of the motion segment unit, leading to instability in the unit and causing severe pain, numbness, decreased mobility, muscle weakness and nerve damage to the patient.

One approach to treating these spinal conditions involves spinal fusion. In spinal fusion, two or more adjacent vertebrae are permanently fused by forming a bony bridge between the vertebrae in order to stabilize and immobilize the motion segment unit. Ligaments, bone, disc, or combinations thereof may be removed prior to fusion. Hardware in the form of bars, plates, rods, screws and cages may be used in combination with bone graft material to facilitate stabilization and fusion of the vertebrae. By placing the adjacent vertebrae in their nominal position and fusing them in place, the relative movement of the vertebrae is eliminated.

Another approach involves the use of spinal devices to stabilize and limit, but not necessarily eliminate, the relative movement of adjacent vertebra. Such devices may include bars, rods, plates, springs, or combinations thereof connecting two sides of a vertebra, the adjacent vertebra of a motion segment unit or both. Although these devices may preserve some mobility of the motion segment units, the devices still impart a certain amount of rigidity to the spine.

A significant problem associated with either approach, but especially spinal fusion, involves the accelerated degeneration of vertebrae and vertebral discs neighboring the stabilized and/or fused motion segment unit. As described above, spinal fusion and stabilization either eliminates or reduces the mobility of one or more motion segment units. As a result, vertebrae and intervertebral discs neighboring the fused or stabilized motion segment unit must accommodate an even greater degree of motion. This added stress can lead to degeneration of the neighboring vertebrae and intervertebral discs. However, stabilization of these vertebrae may delay or eliminate such degeneration. However, stabilization of these neighboring segments may delay or eliminate such degeneration.

SUMMARY

Medical apparatuses for restricting the motion of a vertebra relative to another vertebra and methods for using the apparatuses are provided herein. The apparatuses are designed to protect vertebrae and intervertebral discs from the increased stress and accelerated degeneration induced by neighboring fused or stabilized vertebrae. The medical apparatuses of the present invention comprise a flexible element and a connector configured to secure the ends of the flexible element to a spinal device or to a first vertebra disposed above or below a second vertebra. The flexible element is disposed across at least a portion of the one or more vertebral elements of the second vertebra and is tensioned to restrict the motion of the second vertebra. One or more vertebrae may be disposed between the first and second vertebrae. The first vertebra may be a fused vertebra, a stabilized vertebra or both.

The flexible element may be disposed across at least a portion of one or more vertebral elements of the second vertebra in any manner that restricts the motion of the second vertebra relative to the first vertebra. Vertebral elements may include, but are not limited to, a spinous process, a transverse process, a pedicle, a lamina or an articular process. In some embodiments, the flexible element is disposed across at least a portion of the spinous process and the transverse process of the second vertebra. A variety of materials may be used to form the flexible element, including biologically compatible materials. The shape of the flexible element may vary. In some embodiments, the flexible element comprises a plurality of wires or cables wound or braided together.

A variety of connectors may be used to secure the ends of the flexible element to a vertebra or spinal device. In some embodiments, the connector is a pedicle screw, a polyaxial pedicle screw, a lateral mass screw, a hook or a polyaxial hook. In other embodiments, the connector comprises a bar, a rod, a plate or a housing. The connector may include a fastener for attaching the first connector to the first vertebra or the spinal device. The two ends of the flexible element may be secured to the connector in a variety of ways, including via screws, hooks, pins, welds, clips or snaps or by wrapping or bending the ends of the flexible element around the connector. A variety of materials may be used to form the connectors, including biologically compatible materials such as metals, graphite, ceramics and plastics. Some embodiments of the invention include two connectors, wherein the first connector secures the first end of the flexible element and the second connector secures the second end of the flexible element.

The medical apparatuses of the present invention may include a spinal device. In some embodiments, the spinal device comprises one or more trans-vertebral stabilization elements. The stabilization elements may comprise a rod or a plate. The stabilization elements may be attached to one or more vertebrae via pedicle screws, polyaxial pedicle screws, lateral mass screws, hooks or polyaxial hooks. In some embodiments, the connector for securing the ends of the flexible element is attached to the stabilization element.

The medical apparatuses disclosed herein may further include a tension adjustment element. The tension adjustment element may be attached to the one or more connectors.

Also disclosed herein are methods for using the medical apparatuses. One method comprises the steps of passing the flexible element across the one or more vertebral elements of the second vertebra; securing at least one end of the flexible element to the first connector; and attaching the first connector to the first vertebra or the spinal device. In these embodiments, the flexible element may pass across a variety of vertebral elements of the second vertebra in any manner that restricts the motion of the second vertebra. Another method further comprises adjusting the tension of the flexible element. Yet another method comprises attaching the spinal device to one or more vertebrae.

DETAILED DESCRIPTION

Figure 1:
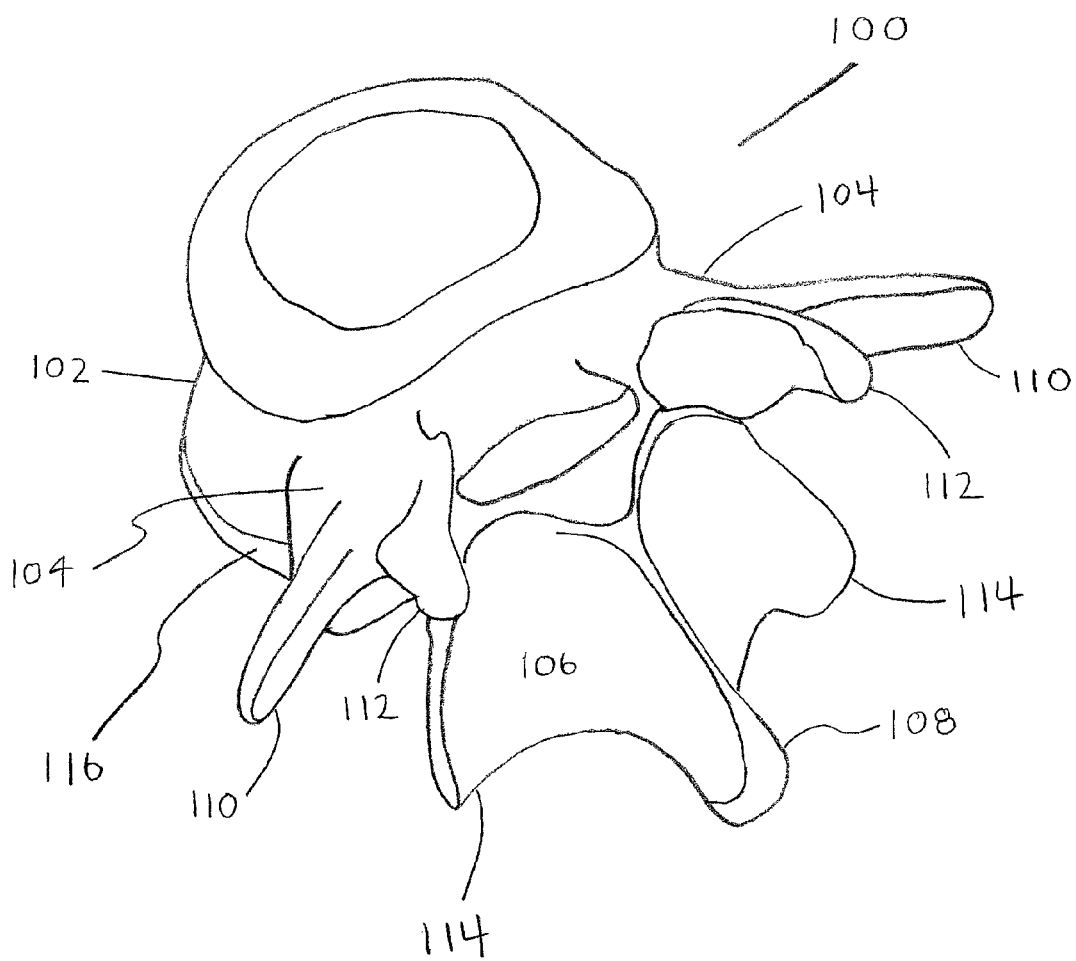
FIG. 1 labels the vertebral elements of a vertebra in a spinal column.

Medical apparatuses for restricting the motion of a vertebra relative to another vertebra and methods for using the apparatuses are provided herein. The apparatuses allow for physiologic motion of a vertebra, while simultaneously restraining the vertebra from excessive movement. The apparatuses provided herein may be used in the cervical, thoracic and lumbar regions of the spine and may be implanted by an open procedure, endoscopically or laprascopically.

The medical apparatuses provided herein comprise a flexible element having two ends and a connector capable of securing the ends of the flexible element to a first vertebra disposed above or below a second vertebra or to a spinal device. The flexible element is disposed across at least a portion of one or more vertebral elements of the second vertebra and is tensioned to restrict the motion of the second vertebra relative to the first vertebra. One or more other vertebrae may be disposed between the first and second vertebrae. In some embodiments, the first vertebra is a fused vertebra. In other embodiments, the first vertebra is a stabilized vertebra. By stabilized vertebra it is meant that the vertebra is attached to a spinal device that serves to stabilize and limit, but not necessarily eliminate, the movement of the vertebra relative to one or more other vertebrae. Examples of such spinal devices are provided below. In still other embodiments, the first vertebra is both a fused and stabilized vertebra.

The flexible element may be disposed across at least a portion of one or more vertebral elements of the second vertebra in any manner that restricts the motion of the second vertebra relative to the first vertebra. For example, the flexible element may loop around the spinous process of the second vertebra. Alternatively, the flexible element may pass underneath and over top of each transverse process, passing underneath the spinous process. In some embodiments, the flexible element may be disposed around the anterior of the second vertebra, passing underneath the transverse processes of the second vertebra. In yet other embodiments, the flexible element may be disposed around the anterior of the second vertebra, passing between each transverse process and superior articular process of the second vertebra. In any of these embodiments, depending upon the exact location of the flexible element, the flexible element may pass across the pedicles, lamina or the inferior articular processes of the second vertebra. Similarly, in any of these embodiments, portions of the flexible element may criss-cross.

The flexible element may comprise a variety of materials provided the flexible element is sufficiently malleable to bend across or wrap around vertebral elements and is sufficiently elastic to stretch as the vertebra moves so that at least some of the physiologic motion of the vertebra is retained. In some embodiments, the flexible element comprises a biologically compatible material. A variety of biologically compatible materials may be used, including, but not limited to, titanium, a titanium alloy, stainless steel, and a polymer. Biologically compatible materials obtained from human and animal tissues, plants and insects such as those described in U.S. Pat. No. 6,752,831 may also be used. The flexible element may also comprise a biocompatible memory metal alloy that exhibits super-elastic properties at body temperature such as disclosed in U.S. Patent Publication No. 2003/0009223.

The tension in the flexible element may be adjusted to limit the flexion, rotation, extension, lateral bending and translation of the second vertebra relative to the first vertebra. Increasing the tension in the element restricts the second vertebra to a smaller degree of motion relative to the first vertebra, while decreasing the tension allows for a greater degree of motion. The tension may be adjusted by forming the flexible element from materials or combinations of materials having different elasticities. Alternatively, the tension may be adjusted by stretching or relaxing the flexible element. For example, stretching the flexible element to increase its length serves to increase the tension in the element, while relaxing the flexible element back to its unstretched length serves to decrease the tension.

The exact shape of the flexible element may vary. In some embodiments, the flexible element may take the form of a single wire or cable or a plurality of wires or cables aligned, wound or braided together. In other embodiments, the flexible element may take the form of a strip or a band. In still other embodiments, the flexible element may take the form of a closed circular structure 204a (see FIG. 2a), much like a rubber band or a "bungee-cord." In such embodiments, the "ends" of the flexible element refer to the locations of the hairpin-like loop 214a (see FIG. 2a) that forms when the closed circular structure 204a is flattened.

Similarly, the exact dimensions of the flexible element may vary. Generally, the thickness of the flexible element will depend upon considerations such as minimizing interference with components of the spinal column, ensuring the flexible element is easily implantable and providing a strong and durable structure. Generally, the length of the flexible element will depend upon the distance the flexible element must span when implanted and the desired tension in the flexible element.

A variety of connectors may be used to secure the ends of the flexible element to a vertebra or spinal device. The connector itself may be a screw, hook or pin that can attach the ends of the flexible element to a vertebra or a spinal device. Suitable screws and hooks include, but are not limited to, pedicle screws, polyaxial pedicle screws, lateral mass screws or polyaxial hooks and the like, such as those disclosed in U.S. Pat. Nos. 5,591,166, 5,628,740, 6,626,908 and U.S. Patent Publication No. 2005/0113927. When attached to a vertebra, the connector may attach to a variety of vertebral elements, including, but not limited to, pedicles, lamina or spinous processes.

In other embodiments, the connector may comprise a distinct piece of hardware, including, but not limited to bars, rods or plates. In such embodiments, the flexible element may be secured to the connector in a variety of ways, including, but not limited to, the screws and hooks described above, or pins, welds, clips, snaps and the like. In other embodiments, the ends of the flexible element may be wrapped around at least a portion of the connector. Alternatively, the connector itself may be bent around the ends of the flexible element. In other related embodiments, the connector may further comprise an opening or aperture for accepting a fastener for attaching the connector to a vertebra or a spinal device. A variety of fasteners may be used to attach the connector to a vertebra or spinal device, including, but not limited to the screws and hooks described above.

The materials used to form the connectors may vary. The connector may comprise a variety of biologically compatible materials, including, but not limited to metals, such as titanium, titanium alloys, chrome cobalt or stainless steel. Other biocompatible materials include graphite and ceramics, such as hydroxapatites. Plastics may also be employed. Suitable plastics include polyethylene (e.g. ultrahigh molecular weight polyethylene) and polyether ester ketone. Similarly, the dimensions of the connectors may vary, provided they are small enough to minimize interference with the components of the spinal column but large enough to secure the ends of the flexible element and to be attached to vertebrae or spinal devices.

Although the embodiments described above make reference to one connector, the medical apparatuses of the present invention may include a plurality of connectors. In some embodiments, two connectors are provided. The first connector secures one end of the flexible element to a vertebra or spinal device, while the second connector secures the opposite end of the flexible element to the vertebra or spinal device. The type of connector, location of attachment to a vertebra, composition and dimensions of each connector may vary as described above.

In some embodiments, the connector secures the ends of the flexible element to a spinal device. In some embodiments, the spinal device comprises one or more trans-vertebral stabilization elements. As such, the stabilizing elements span two or more vertebrae and are located outside of the intervertebral spaces in the spinal column. The stabilizing elements will typically be located at the posterior of the spine, but other placements including lateral and anterior placements are also possible. When only a single stabilizing element is included in the spinal device, it is generally disposed posteriorly to one side of the spinous processes. When two stabilizing elements are included, they are typically disposed in a spaced apart, substantially parallel arrangement wherein one of the stabilizing elements is placed on either side of the spinous processes. In spinal devices including two or more stabilizing elements, the elements optionally may be connected together through a transverse stabilizing element.

The stabilization elements are typically rods or plates having a long dimension that runs along the long dimension of the spine when the stabilizing element is implanted in a patient. Spinal stabilizing rods and plates have been described in the literature, including, but not limited to, the rods described in U.S. Pat. Nos. 6,554,831 and 4,743,260 and the plates described in U.S. Patent Publication 2001/0037111 and U.S. Pat. No. 5,352,224. The stabilizing elements may be adapted to incorporate one or more connecting joints as described in U.S. Patent Publication 2005/0113927.

The stabilization elements may be attached to one or more vertebrae via the screws and hooks described above or via any suitable attaching means capable of securing the stabilization element to a vertebra. Similarly, the stabilization element may comprise any of the materials disclosed above for the connectors.

The following figures show examples of medical apparatuses according to the present invention. The embodiments shown in the figures are intended only to exemplify the invention and should not be construed to limit the invention to any particular embodiment. The drawings are not necessarily to scale and the relative dimensions of the components of the apparatuses provided therein may deviate from those shown in the figures.

Figure 2:
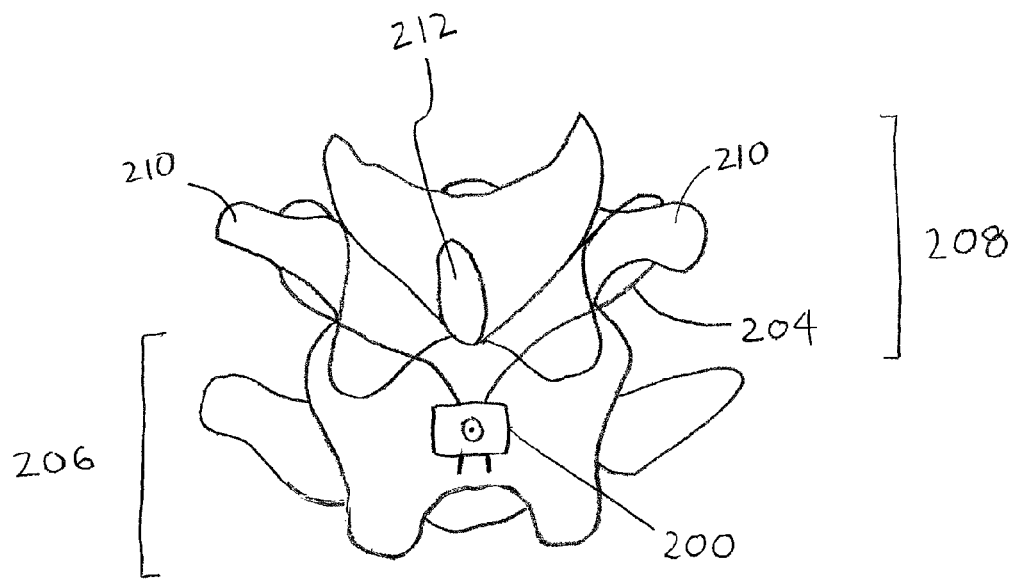
FIG. 2 provides a posterior view of two adjacent vertebrae and a medical apparatus comprising a flexible element and a connector attached to the lower vertebra. The flexible element is disposed across the transverse processes and the spinal process of the upper vertebra.
Figure 3:
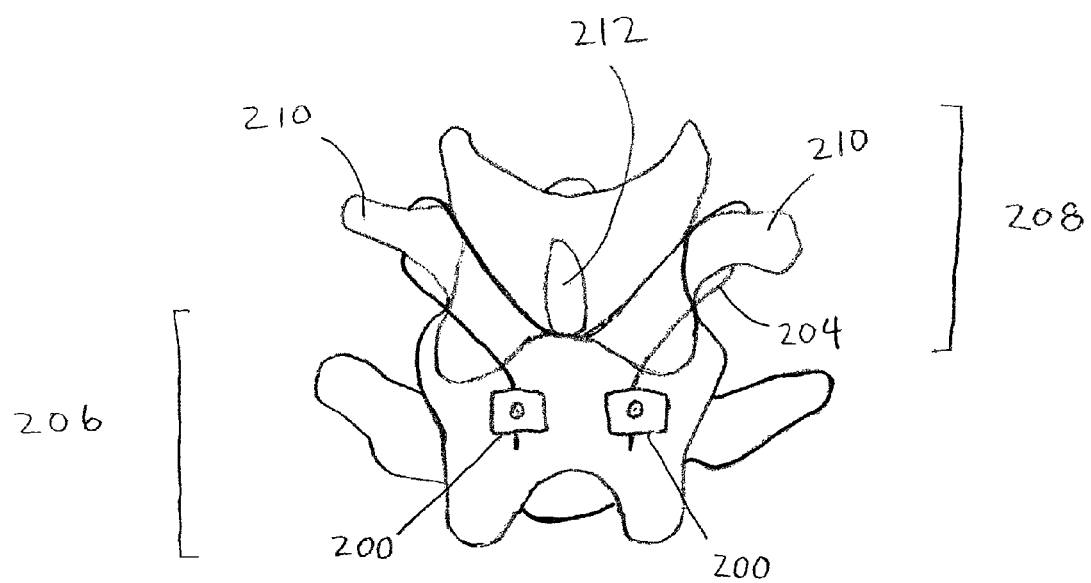
FIG. 3 provides a posterior view of two adjacent vertebrae and a medical apparatus comprising a flexible element and two connectors attached to the lower vertebra. The flexible element is disposed across the transverse processes and the spinal process of the upper vertebra.
Figure 4:
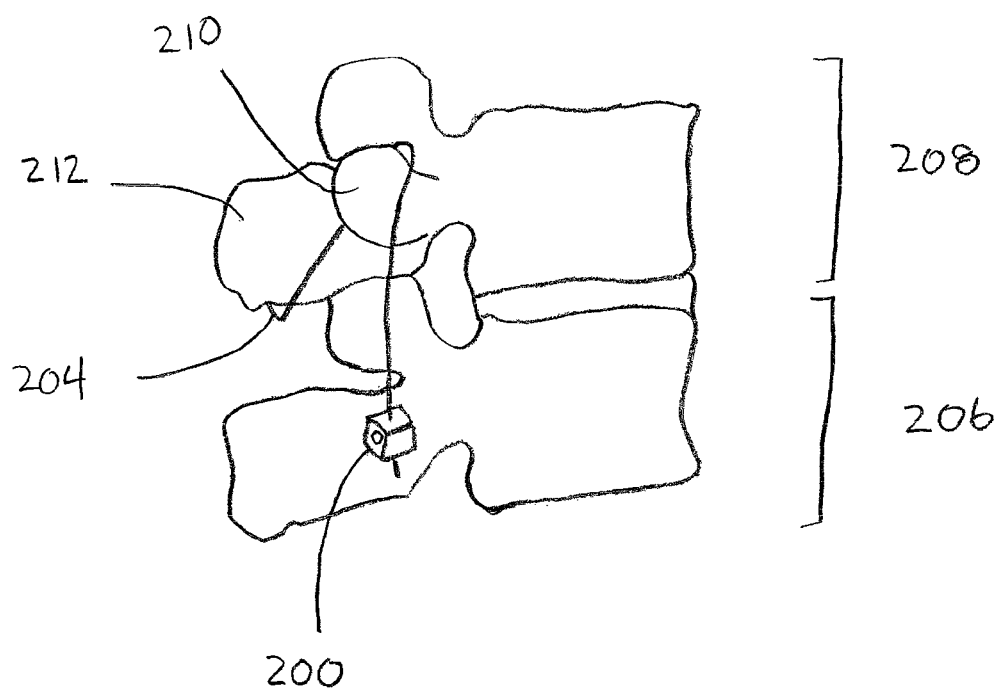
FIG. 4 provides a side view of the embodiment shown in FIG. 3.

FIG. 2 shows a posterior view of two adjacent vertebrae. A single connector 200 secures the ends of the flexible element 204 to a first vertebra 206 disposed below a second vertebra 208. The flexible element 204 passes underneath and in front of the transverse processes 210 and under the spinous process 212 of the second vertebra 208. FIG. 3 shows an embodiment of the invention with two connectors 200. FIG. 4 shows a side view of the embodiment of FIG. 3.

Figure 2A:
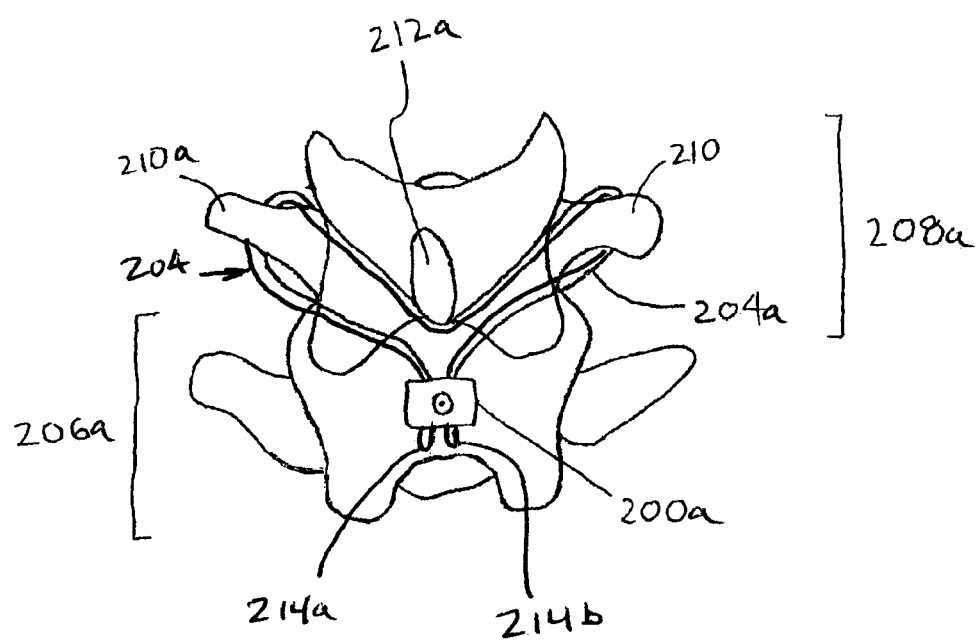
FIG. 2a provides a posterior view of two adjacent vertebrae and a medical apparatus comprising another flexible element having a closed circular structure and a connector attached to the lower vertebra. The flexible element is disposed across the transverse processes and the spinal process of the upper vertebra.

FIG. 2a shows a posterior view of two adjacent vertebrae. A single connector 200a secures the first and second ends 214a of the flexible element in the form of a closed circular structure 204a to a first vertebra 206a disposed below a second vertebra 208a. The flexible element in the form of a closed circular structure 204a passes underneath and in front of the transverse processes 210a and under the spinous process 212a of the second vertebra 208a.

Figure 5A:
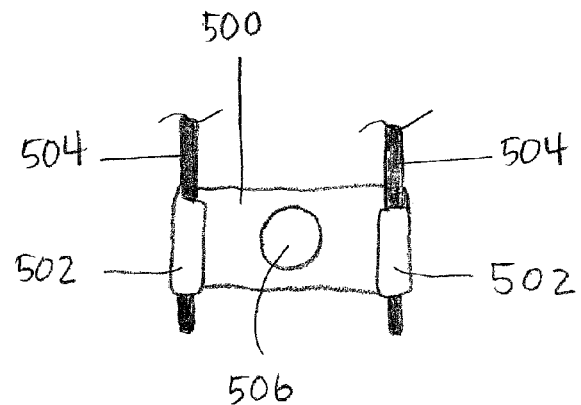
FIGS. 5A-5C show a variety of connectors for securing the ends of a flexible element to a vertebra or a spinal device.
Figure 5B:
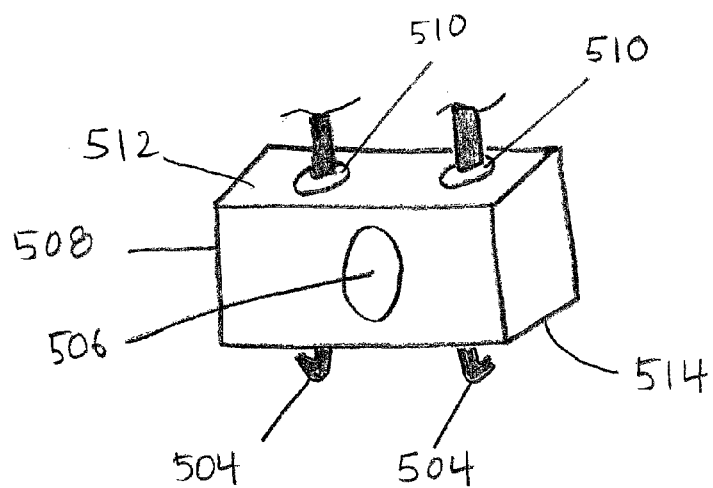
Figure 5C:
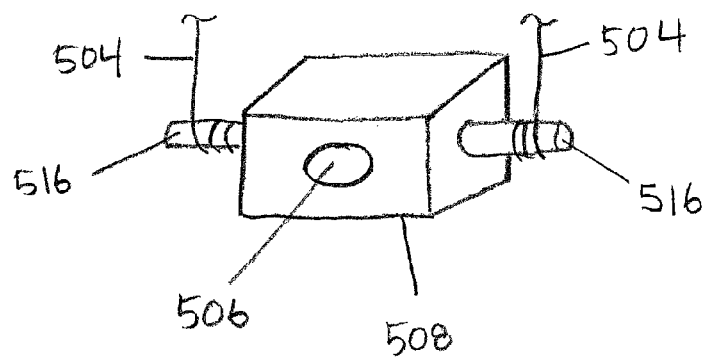

FIGS. 5A-5C show various connectors according to the present invention. In the embodiment shown in FIG. 5A, the connector comprises a bar 500. In some embodiments, the sides 502 of the bar may be bent or crimped over ends 504 of the flexible element. An aperture 506 may be provided, through which a fastener may pass to attach the connector to a vertebra or a spinal device. In another embodiment shown in FIG. 5B, the connector comprises a housing 508. Channels 510 may be provided in the housing, allowing the ends of the flexible element 504 to pass through the top 512 and bottom 514 of the housing. The ends of the flexible element may be bent or knotted to prevent each end from passing back through the channels 510. Alternatively, any piece having a dimension larger than the dimensions of the channels may be attached to the ends of the flexible element to prevent each end from passing back through the channels. In the embodiment shown in FIG. 5C, the housing comprises one or more rods 516 extending from the ends of the housing. The ends of the flexible element 504 may be secured to the housing by wrapping the ends around the rods.

Figure 6:
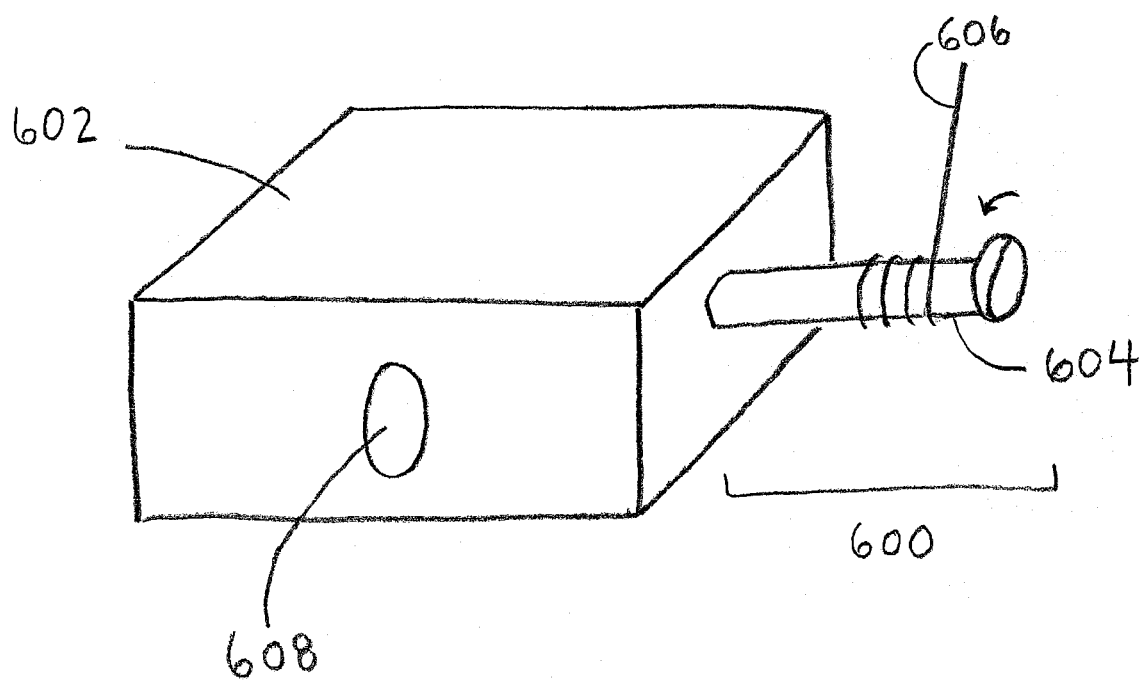
FIG. 6 shows a connector comprising a tension adjustment element.

In other embodiments of the present invention, the medical apparatus comprises a tension adjustment element. The tension adjustment element 600 may be included on one or more connectors 602 as shown in FIG. 6. The tension adjustment element comprises a rotating rod 604 extending outwardly from the side of the connector 602. One end of the flexible element 606 is attached to the rotating rod so that upon rotation, the flexible element is wound or unwound around the rod. Because the other end of the flexible element is also fixed to the connector 602 or to a separate, second connector, winding the flexible element stretches the element, increasing the tension in the element. Unwinding the flexible element relaxes the element, decreasing the tension. The tension adjustment element may be a screw that screws into and unscrews out of the connector through a tapped bore. The portion of the screw contacting the end of the flexible element may comprise a groove to accommodate the flexible element, ensuring that the flexible element smoothly winds and unwinds as the screw is rotated. As with other connectors, the connector 602 may include an aperture 608, through which a fastener may pass to attach the connector to a vertebra or a spinal device.

Figure 7:
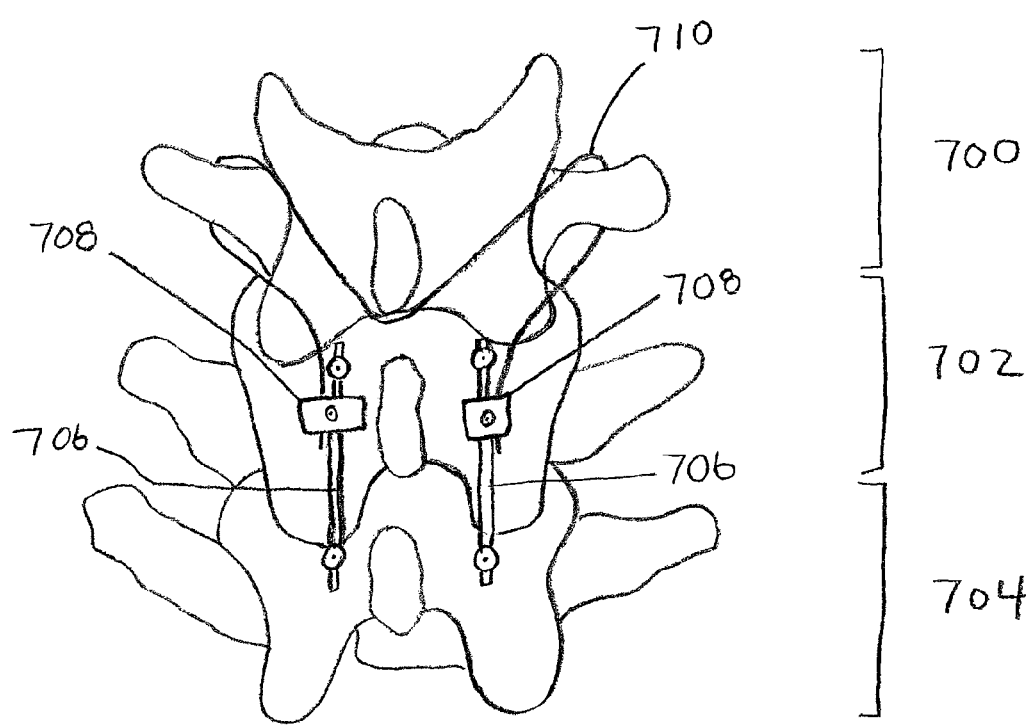
FIG. 7 provides a posterior view of two adjacent vertebrae and a medical apparatus comprising a flexible element, a spinal device comprising two stabilization elements attached to the middle and lower vertebrae, and two connectors attached to the spinal device. The flexible element is disposed across the transverse processes and the spinal process of the upper vertebra.

FIG. 7 shows a posterior view of three adjacent vertebrae, 700, 702 and 704. A spinal device comprising two transvertebral stabilization elements 706 is attached to vertebrae 702 and 704. The stabilizations elements 706 are spaced apart on either side of the spinous processes. Connectors 708 are attached to each of the stabilization elements 706 and may be positioned at any point along the length of the stabilization elements. The connectors 708 secure the ends of the flexible element 710 to each of the stabilization elements 706. The flexible element 710 is disposed across at least a portion of the transverse processes and the spinous process of the vertebra 700 as shown in FIGS. 2-4.

In another aspect of the invention, methods of using the medical apparatuses disclosed herein are provided. One method comprises the steps of passing the flexible element across the one or more vertebral elements of the second vertebra; securing at least one end of the flexible element to the first connector; and attaching the first connector to the first vertebra or the spinal device. In these embodiments, the flexible element may pass across a variety of vertebral elements of the second vertebra in any manner that restricts the motion of the second vertebra as described above. Another method further comprises attaching a second connector to the first vertebra or the spinal device and securing the other end of the flexible element to the second connector.

In yet another method, the method further comprises adjusting the tension of the flexible element. The tension may be adjusted in a variety of ways as described above. In some embodiments, the medical apparatus comprises a tension adjustment element. In such embodiments, the tension adjustment element may be attached to the connector and may include a rotating rod. In such embodiments, the step of adjusting the tension of the flexible element may comprise attaching one end of the flexible element to the rotating rod and rotating the rod wind or unwind the flexible element around the rod.

In yet another method, the method further comprises attaching the spinal device to one or more vertebrae. In some embodiments, the spinal device comprises one or more transvertebral stabilization elements as described above. In such embodiments, the method comprises attaching the stabilization element to one or more vertebrae and attaching the connector to the stabilization element.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

For the purposes of this disclosure and unless otherwise specified, "a" or "an" means "one or more." All patents, applications, references and publications cited herein are incorporated by reference in their entirety to the same extent as if they were individually incorporated by reference.

While some detailed embodiments have been illustrated and described, it should be understood that such detailed embodiments are merely exemplary and changes and modifications can be made therein in accordance with ordinary skill in the art without departing from the invention in its broader aspects as defined in the following claims.

The invention claimed is:

1. A medical apparatus comprising:
an elongated flexible element in the form of a closed circular structure, and having a first end and a second end formed by hairpin loops when the closed circular structure is flattened, and a mid-portion between the first end and the second end;
a single first connector configured to secure the hairpin loops of the first end and the second end of the elongated flexible element to a first vertebra;
wherein the first vertebra is disposed above or below a second vertebra;
the first and second vertebrae comprising a first transverse process and a second transverse process and a spinous process;
the mid-portion of the elongated flexible element is configured to be disposed at least partially around the first transverse process and the second transverse process and beneath the spinous process of the second vertebra, and a tension in the elongated flexible element is adjustable to restrict the motion of the second vertebra;
wherein the elongated flexible element is formed from a combination of materials having different elasticities, so that the tension in the elongated flexible element can be adjusted.

2. The medical apparatus of claim 1, wherein the mid-portion of the elongated flexible element is configured to be wrapped around the transverse processes of the second vertebra.

3. The medical apparatus of claim 1, wherein the elongated flexible element comprises a biologically compatible material selected from the group consisting of titanium, a titanium alloy, stainless steel, and a polymer.

4. The medical apparatus of claim 1, wherein the elongated flexible element comprises a plurality of wires or cables wound or braided together.

5. The medical apparatus of claim 1, wherein the first connector comprises a bar, a rod, a plate, a housing, or a fastener for attaching the first connector to the first vertebra.

6. The medical apparatus of claim 1, wherein the two ends of the elongated flexible element are secured to the first connector via screws, hooks, pins, welds, clips, snaps, or by wrapping or bending the ends of the elongated flexible element around the first connector.

7. The medical apparatus of claim 1, wherein the spinal device comprises one or more trans-vertebral stabilization elements.

8. The medical apparatus of claim 7, wherein the trans-vertebral stabilization element comprises a rod or a plate.

9. The medical apparatus of claim 7, wherein the trans-vertebral stabilization element is attached to one or more vertebrae via pedicle screws, polyaxial pedicle screws, lateral mass screws, hooks or polyaxial hooks and the first connector is attached to the trans-vertebral stabilization element.

10. The medical apparatus of claim 1, further comprising a tension adjustment element attached to the first connector.

* * * * *